United States Patent [19]

Hosokawa et al.

[11] Patent Number: 5,990,287
[45] Date of Patent: Nov. 23, 1999

[54] HUMAN MONOCLONAL ANTIBODY SPECIFICALLY BINDING TO SURFACE ANTIGEN OF CANCER CELL MEMBRANE

[75] Inventors: Saiko Hosokawa, Kawasaki; Toshiaki Tagawa, Yokohama; Yoko Hirakawa, Yokohama; Norihiko Ito, Yokohama; Kazuhiro Nagaike, Sagamihara, all of Japan

[73] Assignee: Mitsubishi Chemical Corporation, Tokyo, Japan

[21] Appl. No.: 09/017,628

[22] Filed: Feb. 2, 1998

Related U.S. Application Data

[62] Division of application No. 08/360,125, Dec. 20, 1994, Pat. No. 5,767,246, which is a continuation of application No. 07/905,534, Jun. 29, 1992.

[30] Foreign Application Priority Data

Jun. 28, 1991  [JP]  Japan  .................................... 3-158859
Jun. 28, 1991  [JP]  Japan  .................................... 3-158860
Jun. 28, 1991  [JP]  Japan  .................................... 3-158861

[51] Int. Cl.$^6$ .......................... C07K 16/30; C07K 16/18; C07K 16/28
[52] U.S. Cl. .................................... 530/388.8; 530/387.1; 530/387.7; 530/388.15; 530/389.7; 530/866
[58] Field of Search .......................... 530/387.1, 387.7, 530/388.15, 388.8, 389.7, 866

[56] References Cited

U.S. PATENT DOCUMENTS

| 4,800,155 | 1/1989 | Taniguchi et al. ....................... 435/7.23 |
| 5,264,221 | 11/1993 | Tagawa et al. ........................... 424/450 |

FOREIGN PATENT DOCUMENTS

| 0 178 891 | 9/1987 | European Pat. Off. . |
| 9014595 | 11/1990 | WIPO . |
| 9109134 | 6/1991 | WIPO . |
| 9116071 | 10/1991 | WIPO . |

OTHER PUBLICATIONS

Cancer Research vol. 45, 263–271, Jan. 1985, Imam et al., Generation and Immunohistological Characterization of Human Monoclonal Antibodies to Mammary Carcinoma Cells.
Cancer Immunol/Immunotherapy (1989) 28: 296–300, Formenti et al., "Reactivity of a Human Monoclonal Antibody Against Carcinomas and other Lesions of the Colon".
Cancer Research vol. 49, 2471–2476, May 1, 1989, Vollmers et al., "SC–1 a Functional Human Monoclonal Antibody Against Autologous Stomach Carcinoma Cells".
Cell vol. 22, 197–207, Nov. 1980, Hieter et al. "Cloned Human and Mouse Kappa Immunoglobulin Constant and J Region Genes Conserve Homology in Functional Segments".
Nature vol. 294, 536–540, Hieter et al., "Clustered Arrangement of Immunoglobulin Constant Region Genes in Man" Dec. 10, 1981.
The Journal of Biological Chemistry vol. 257, 1516–1522, Feb. 1992, Hieter et al., "Evolution of Human Immunoglobulin k J Region Genes".
Nucleic Acids Research, vol. 14, 1779–1789, Huck et al., Sequence of a human immunoglobulin Gamma 3 heavy chain constant region gene: comparison with the other human C genes (1986).
Nucleic Acids Research, vol. 18, 4278, May 1990, Friedlander et al., Complete nucleotide sequence of the membrane form of the human IgM heavy chain.
Nature vol. 321, 522–525, May 1986, Jones et al., "Replacing the complementarity determining regions in a human antibody with those from a mouse".
Chen et al., J. Cancer Res. Clin. Oncol., 117 (4), pp. 367–376, 1991.
Liu et al., Chung Hug Chung Liv Tsu Chih, 10(4), pp. 242–244, 1988.
Harris et al., TIBTECH, 11, pp. 42–44, 1993.
Dermer, Bio/Technology, 12, p. 320, 1994.
Hird et al., Chapter 12, from: Genes and Cancer, Ed. D. Carney, et al., Wiley and Sons, pp. 183–189, 1990.
Saito et al., J. Natl. Cancer Institute 80(10), pp. 728–738, 1988.
Waldman, Science, vol. 262, pp. 1657–1662, 1991.
Parks et al., Chapter 29, From Handbook of Exp. Immunol. vol. 1, Immunochemistry, Blackwell Scientific Pub, 1986.
Chemical Abstracts, vol. 111, No. 13, Sep. 25, 1989 Kazuhiro Yoshikawa et al. "A Human Monoclonal Antibody Recognizing a Surface Antigen on Stomach Cancer Cells.", p. 503, Col. 2, Abstract–No. 113 362y.
Chemical Abstracts, vol. 100, No. 21, May 21, 1984 Takashi Masuko et al. "Monoclonal Antibodies Against Cell Surface Antigens Present on Human Urinary Bladder Cancer Cells.", p. 474, Col. 1, Abstract–No. 172 850b.

*Primary Examiner*—Ronald B. Schwadron
*Attorney, Agent, or Firm*—Wenderoth, Lind & Ponack, L.L.P.

[57] ABSTRACT

A human monoclonal antibody specifically binding to a surface antigen of cancer cell membrane, an isolated DNA encoding the antibody, and a hybridoma producing the antibody. An anti-cancer formulation comprising the monoclonal antibody bonded to the surface of a liposome enclosing an anti-cancer agent or toxin is also provided.

3 Claims, 4 Drawing Sheets

SEQUENCE LISTING

<160> NUMBER OF SEQ ID NOS: 42

<210> SEQ ID NO 1
<211> LENGTH: 37
<212> TYPE: DNA
<213> ORGANISM: human IgG antibody

<400> SEQUENCE: 1
ggcccttggt ggaggctgaa gagacggtga ccattct                                37

<210> SEQ ID NO 2
<211> LENGTH: 21
<212> TYPE: DNA
<213> ORGANISM: human IgG antibody

<400> SEQUENCE: 2
tggtgcagcc acagttcgtt t                                                 21

<210> SEQ ID NO 3
<211> LENGTH: 357
<212> TYPE: DNA
<213> ORGANISM: Unknown
<220> FEATURE:
<223> OTHER INFORMATION: Hybridoma producing human antibody GAH

<400> SEQUENCE: 3
caggtgcagc tgcaggagtc gggcccagga ctggtgaagc cttcacagac cctgtccctc        60
acctgcactg tctctggtgg ctccatcagc agttgtggtt tctactggaa ctggatccgc       120
cagcacccag ggaagggcct ggagtggatt gggtacatct attacagtgg gagcacctac       180
tacaacccgt ccctcaagag tcgagttacc atatcgctag acacgtctaa gagccagttc       240
tccctgaagc tgagctctct gactgccgcg gacacggccg tgtattactg tgcgaggtct       300
acccgactac ggggggctga ctactggggc cagggaacaa tggtcaccgt ctcttca         357

<210> SEQ ID NO 4
<211> LENGTH: 342
<212> TYPE: DNA
<213> ORGANISM: Unknown
<220> FEATURE:
<223> OTHER INFORMATION: Hybridoma producing human antibody GAH

<400> SEQUENCE: 4
gacatcgtga tgacccagtc tccagactcc ctggctgtgt ctctgggcga gagggccacc        60
atcaactgca gtccagcca gagtgtttta tacaactcca acaataagaa atacttagct       120
tggtaccagc agaaaccagg acagcctcct aagctgctca tttactgggc atctacccgg       180
gaatccgggg tccctgaccg attcagtggc agcgggtctg ggacagattt cactctcacc       240
atcagcagcc tgcaggctga agatgtggca gtttattact gtcagcagta ttatagtact       300
ccgtggacgt tcggccaagg gaccaaggtg gaaatcaaac ga                         342

<210> SEQ ID NO 5
<211> LENGTH: 119
<212> TYPE: PRT
<213> ORGANISM: Unknown
<220> FEATURE:
<223> OTHER INFORMATION: Hybridoma producing human antibody GAH

<400> SEQUENCE: 5

Gln Val Gln Leu Gln Glu Ser Gly Pro Gly Leu Val Lys Pro Ser Gln
 1               5                  10                  15

```
Thr Leu Ser Leu Thr Cys Thr Val Ser Gly Gly Ser Ile Ser Ser Cys
                20                  25                  30

Gly Phe Tyr Trp Asn Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
     50                  55                  60

Leu Lys Ser Arg Val Thr Ile Ser Leu Asp Thr Ser Lys Ser Gln Phe
 65                  70                  75                  80

Ser Leu Lys Leu Ser Ser Leu Thr Ala Ala Asp Thr Ala Val Tyr Tyr
                 85                  90                  95

Cys Ala Arg Ser Thr Arg Leu Arg Gly Ala Asp Tyr Trp Gly Gln Gly
                100                 105                 110

Thr Met Val Thr Val Ser Ser
            115
```

<210> SEQ ID NO 6
<211> LENGTH: 114
<212> TYPE: PRT
<213> ORGANISM: Unknown
<220> FEATURE:
<223> OTHER INFORMATION: Hybridoma producing human antibody GAH

<400> SEQUENCE: 6

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Asn
             20                  25                  30

Ser Asn Asn Lys Lys Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Trp Thr Phe Gly Gln Gly Thr Lys Val Glu Ile
                100                 105                 110

Lys Arg
```

<210> SEQ ID NO 7
<211> LENGTH: 17
<212> TYPE: DNA
<213> ORGANISM: human IgM antibody

<400> SEQUENCE: 7 cgaggggaa aagggtt                                                    17

<210> SEQ ID NO 8
<211> LENGTH: 19
<212> TYPE: DNA
<213> ORGANISM: human IgM antibody

<400> SEQUENCE: 8
gaagctcctc agaggaggg                                                 19

<210> SEQ ID NO 9
<211> LENGTH: 366
<212> TYPE: DNA
<213> ORGANISM: Unknown

<220> FEATURE:
<223> OTHER INFORMATION: Hybridoma producing human antibody 1-3-1

<400> SEQUENCE: 9

```
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag gaaggggct ggagtggatt gggagtatct attatagtgg gagcacctac      180
tacaacccgt ccctcaagag tcgagtcacc atatccgtag acacgtccaa gaaccagttc     240
tccctgaagc tgagctctgt gaccgccgca gacacggctg tgtattactg tgcgaggggg     300
agctacgggg gctactacta cggtatggac gtctggggcc aagggaccac ggtcaccgtc     360
tcctca                                                                366
```

<210> SEQ ID NO 10
<211> LENGTH: 324
<212> TYPE: DNA
<213> ORGANISM: Unknown
<220> FEATURE:
<223> OTHER INFORMATION: Hybridoma producing human antibody 1-3-1

<400> SEQUENCE: 10

```
tatgagctga cacagccacc ctcggtgtca gtgtccccag acagacggc caggatcacc       60
tgctctggag atgcattgcc aaagcaatat gcttattggt accagcagaa gccaggccag     120
gcccctgtgc tggtgatata taagacagt gagaggccct cagggatccc tgagcgattc      180
tctggctcca gctcagggac aacagtcacg ttgaccatca gtggagtcca ggcagaagac     240
gaggctgact attactgtca atcagcagac agcagtggta cttatgaggt attcggcgga     300
gggaccaagc tgaccgtcct aggt                                            324
```

<210> SEQ ID NO 11
<211> LENGTH: 122
<212> TYPE: PRT
<213> ORGANISM: Unknown
<220> FEATURE:
<223> OTHER INFORMATION: Hybridoma producing human antibody 1-3-1

<400> SEQUENCE: 11

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
     50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                85                  90                  95

Cys Ala Arg Gly Ser Tyr Gly Gly Tyr Tyr Tyr Gly Met Asp Val Trp
            100                 105                 110

Gly Gln Gly Thr Thr Val Thr Val Ser Ser
        115                 120
```

<210> SEQ ID NO 12
<211> LENGTH: 108
<212> TYPE: PRT
<213> ORGANISM: Unknown

-continued

```
<220> FEATURE:
<223> OTHER INFORMATION: Hybridoma producing human antibody 1-3-1

<400> SEQUENCE: 12

Tyr Glu Leu Thr Gln Pro Pro Ser Val Ser Val Ser Pro Gly Gln Thr
 1               5                  10                  15

Ala Arg Ile Thr Cys Ser Gly Asp Ala Leu Pro Lys Gln Tyr Ala Tyr
             20                  25                  30

Trp Tyr Gln Gln Lys Pro Gly Gln Ala Pro Val Leu Val Ile Tyr Lys
         35                  40                  45

Asp Ser Glu Arg Pro Ser Gly Ile Pro Glu Arg Phe Ser Gly Ser Ser
     50                  55                  60

Ser Gly Thr Thr Val Thr Leu Thr Ile Ser Gly Val Gln Ala Glu Asp
65                  70                  75                  80

Glu Ala Asp Tyr Tyr Cys Gln Ser Ala Asp Ser Ser Gly Thr Tyr Glu
                 85                  90                  95

Val Phe Gly Gly Gly Thr Lys Leu Thr Val Leu Gly
            100                 105

<210> SEQ ID NO 13
<211> LENGTH: 8
<212> TYPE: PRT
<213> ORGANISM: Unknown
<220> FEATURE:
<223> OTHER INFORMATION: Hybridoma producing human monoclonal antibody,
      an antigen to which exists on the surface of cancer cell membrane
<220> FEATURE:
<223> OTHER INFORMATION: Xaa at 4:  can be Cys or Ser, Xaa at 5:  can be
      Gly or Ser, Xaa at 6:  can be Phe or Tyr

<400> SEQUENCE: 13

Ile Ser Ser Xaa Xaa Xaa Tyr Trp
 1               5

<210> SEQ ID NO 14
<211> LENGTH: 12
<212> TYPE: PRT
<213> ORGANISM: Unknown
<220> FEATURE:
<223> OTHER INFORMATION: Hybridoma producing human monoclonal antibody,
      an antigen to which exists on the surface of cancer cell membrane
<220> FEATURE:
<223> OTHER INFORMATION: Xaa at 3:  can be Tyr or Ser

<400> SEQUENCE: 14

Ile Gly Xaa Ile Tyr Tyr Ser Gly Ser Thr Tyr Tyr
 1               5                  10

<210> SEQ ID NO 15
<211> LENGTH: 4
<212> TYPE: PRT
<213> ORGANISM: Unknown
<220> FEATURE:
<223> OTHER INFORMATION: Hybridoma producing human monoclonal antibody,
      an antigen to which exists on the surface of cancer cell membrane
<220> FEATURE:
<223> OTHER INFORMATION: Xaa at 2:  can be Ala or Met, Xaa at 4:  can be
      Tyr or Val

<400> SEQUENCE: 15

Gly Xaa Asp Xaa
 1

<210> SEQ ID NO 16
<211> LENGTH: 9
<212> TYPE: PRT
```

<213> ORGANISM: Unknown
<220> FEATURE:
<223> OTHER INFORMATION: Hybridoma producing human antibody GAH

<400> SEQUENCE: 16

Ile Ser Ser Cys Gly Phe Tyr Trp Asn
1               5

<210> SEQ ID NO 17
<211> LENGTH: 12
<212> TYPE: PRT
<213> ORGANISM: Unknown
<220> FEATURE:
<223> OTHER INFORMATION: Hybridoma producing human antibody GAH

<400> SEQUENCE: 17

Ile Gly Tyr Ile Tyr Tyr Ser Gly Ser Thr Tyr Tyr
1               5                   10

<210> SEQ ID NO 18
<211> LENGTH: 9
<212> TYPE: PRT
<213> ORGANISM: Unknown
<220> FEATURE:
<223> OTHER INFORMATION: Hybridoma producing human antibody GAH

<400> SEQUENCE: 18

Ser Thr Arg Leu Arg Gly Ala Asp Tyr
1               5

<210> SEQ ID NO 19
<211> LENGTH: 17
<212> TYPE: PRT
<213> ORGANISM: Unknown
<220> FEATURE:
<223> OTHER INFORMATION: Hybridoma producing human antibody GAH

<400> SEQUENCE: 19

Lys Ser Ser Gln Ser Val Leu Tyr Asn Ser Asn Asn Lys Lys Tyr Leu
1               5                   10                  15
Ala

<210> SEQ ID NO 20
<211> LENGTH: 7
<212> TYPE: PRT
<213> ORGANISM: Unknown
<220> FEATURE:
<223> OTHER INFORMATION: Hybridoma producing human antibody GAH

<400> SEQUENCE: 20

Trp Ala Ser Thr Arg Glu Ser
1               5

<210> SEQ ID NO 21
<211> LENGTH: 9
<212> TYPE: PRT
<213> ORGANISM: Unknown
<220> FEATURE:
<223> OTHER INFORMATION: Hybridoma producing human antibody GAH

<400> SEQUENCE: 21

Gln Gln Tyr Tyr Ser Thr Pro Trp Thr
1               5

<210> SEQ ID NO 22
<211> LENGTH: 10
<212> TYPE: PRT

<213> ORGANISM: Unknown
<220> FEATURE:
<223> OTHER INFORMATION: Hybridoma producing human antibody 1-3-1

<400> SEQUENCE: 22

Ile Ser Ser Ser Ser Tyr Tyr Trp Gly Trp
 1               5                  10

<210> SEQ ID NO 23
<211> LENGTH: 14
<212> TYPE: PRT
<213> ORGANISM: Unknown
<220> FEATURE:
<223> OTHER INFORMATION: Hybridoma producing human antibody 1-3-1

<400> SEQUENCE: 23

Ile Gly Ser Ile Tyr Tyr Ser Gly Ser Thr Tyr Tyr Asn Pro
 1               5                  10

<210> SEQ ID NO 24
<211> LENGTH: 12
<212> TYPE: PRT
<213> ORGANISM: Unknown
<220> FEATURE:
<223> OTHER INFORMATION: Hybridoma producing human antibody 1-3-1

<400> SEQUENCE: 24

Gly Ser Tyr Gly Gly Tyr Tyr Gly Met Asp Val
 1               5                  10

<210> SEQ ID NO 25
<211> LENGTH: 9
<212> TYPE: PRT
<213> ORGANISM: Unknown
<220> FEATURE:
<223> OTHER INFORMATION: Hybridoma producing human antibody 1-3-1

<400> SEQUENCE: 25

Asp Ala Leu Pro Lys Gln Tyr Ala Tyr
 1               5

<210> SEQ ID NO 26
<211> LENGTH: 4
<212> TYPE: PRT
<213> ORGANISM: Unknown
<220> FEATURE:
<223> OTHER INFORMATION: Hybridoma producing human antibody 1-3-1

<400> SEQUENCE: 26

Lys Asp Ser Glu
 1

<210> SEQ ID NO 27
<211> LENGTH: 11
<212> TYPE: PRT
<213> ORGANISM: Unknown
<220> FEATURE:
<223> OTHER INFORMATION: Hybridoma producing human antibody 1-3-1

<400> SEQUENCE: 27

Gln Ser Ala Asp Ser Ser Gly Thr Tyr Glu Val
 1               5                  10

<210> SEQ ID NO 28
<211> LENGTH: 24
<212> TYPE: DNA
<213> ORGANISM: Unknown
<220> FEATURE:

<223> OTHER INFORMATION: Hybridoma producing human monoclonal antibody, an antigen to which exists on the surface of cancer cell membrane
<220> FEATURE:
<223> OTHER INFORMATION: n at 10: can be T or A, n at 13: can be G or A, n at 17 can be T or A

<400> SEQUENCE: 28
atcagcagtn gtngttncta ctgg                     24

<210> SEQ ID NO 29
<211> LENGTH: 36
<212> TYPE: DNA
<213> ORGANISM: Unknown
<220> FEATURE:
<223> OTHER INFORMATION: Hybridoma producing human monoclonal antibody, an antigen to which exists on the surface of cancer cell membrane
<220> FEATURE:
<223> OTHER INFORMATION: n at 7: can be T or A, n at 8: can be A or G, n at 9: can be C or T, n at 18: can be C or T

<400> SEQUENCE: 29
attgggnnna tctattanag tgggagcacc tactac          36

<210> SEQ ID NO 30
<211> LENGTH: 12
<212> TYPE: DNA
<213> ORGANISM: Unknown
<220> FEATURE:
<223> OTHER INFORMATION: Hybridoma producing human monoclonal antibody, an antigen to which exists on the surface of cancer cell membrane
<220> FEATURE:
<223> OTHER INFORMATION: n at 3: can be G or T, n at 4: can be G or A, n at 5: can be C or T, n at 6: can be G or T, n at 10: can be G or T, n at 11: can be A or T

<400> SEQUENCE: 30
ggnnnngacn nc                                  12

<210> SEQ ID NO 31
<211> LENGTH: 24
<212> TYPE: DNA
<213> ORGANISM: Unknown
<220> FEATURE:
<223> OTHER INFORMATION: Hybridoma producing human antibody GAH

<400> SEQUENCE: 31
atcagcagtt gtggtttcta ctgg                     24

<210> SEQ ID NO 32
<211> LENGTH: 36
<212> TYPE: DNA
<213> ORGANISM: Unknown
<220> FEATURE:
<223> OTHER INFORMATION: Hybridoma producing human antibody GAH

<400> SEQUENCE: 32
attgggtaca tctattacag tgggagcacc tactac          36

<210> SEQ ID NO 33
<211> LENGTH: 27
<212> TYPE: DNA
<213> ORGANISM: Unknown
<220> FEATURE:
<223> OTHER INFORMATION: Hybridoma producing human antibody GAH

<400> SEQUENCE: 33
tctacccgac tacgggggc tgactac                   27

<210> SEQ ID NO 34
<211> LENGTH: 51
<212> TYPE: DNA
<213> ORGANISM: Unknown
<220> FEATURE:
<223> OTHER INFORMATION: Hybridoma producing human antibody GAH

<400> SEQUENCE: 34
aagtccagcc agagtgtttt atacaactcc aacaataaga aatacttagc t          51

<210> SEQ ID NO 35
<211> LENGTH: 21
<212> TYPE: DNA
<213> ORGANISM: Unknown
<220> FEATURE:
<223> OTHER INFORMATION: Hybridoma producing human antibody GAH

<400> SEQUENCE: 35
tgggcatcta cccgggaatc c                                           21

<210> SEQ ID NO 36
<211> LENGTH: 27
<212> TYPE: DNA
<213> ORGANISM: Unknown
<220> FEATURE:
<223> OTHER INFORMATION: Hybridoma producing human antibody GAH

<400> SEQUENCE: 36
cagcagtatt atagtactcc gtggacg                                     27

<210> SEQ ID NO 37
<211> LENGTH: 30
<212> TYPE: DNA
<213> ORGANISM: Unknown
<220> FEATURE:
<223> OTHER INFORMATION: Hybridoma producing human antibody 1-3-1

<400> SEQUENCE: 37
atcagcagta gtagttacta ctggggctgg                                  30

<210> SEQ ID NO 38
<211> LENGTH: 42
<212> TYPE: DNA
<213> ORGANISM: Unknown
<220> FEATURE:
<223> OTHER INFORMATION: Hybridoma producing human antibody 1-3-1

<400> SEQUENCE: 38
attgggagta tctattatag tgggagcacc tactacaacc cg                    42

<210> SEQ ID NO 39
<211> LENGTH: 36
<212> TYPE: DNA
<213> ORGANISM: Unknown
<220> FEATURE:
<223> OTHER INFORMATION: Hybridoma producing human antibody 1-3-1

<400> SEQUENCE: 39
gggagctacg ggggctacta ctacggtatg gacgtc                           36

<210> SEQ ID NO 40
<211> LENGTH: 27
<212> TYPE: DNA
<213> ORGANISM: Unknown
<220> FEATURE:
<223> OTHER INFORMATION: Hybridoma producing human antibody 1-3-1

<400> SEQUENCE: 40

```
gatgcattgc caaagcaata tgcttat                                          27

<210> SEQ ID NO 41
<211> LENGTH: 12
<212> TYPE: DNA
<213> ORGANISM: Unknown
<220> FEATURE:
<223> OTHER INFORMATION: Hybridoma producing human antibody 1-3-1

<400> SEQUENCE: 41
aaagacagtg ag                                                          12

<210> SEQ ID NO 42
<211> LENGTH: 33
<212> TYPE: DNA
<213> ORGANISM: Unknown
<220> FEATURE:
<223> OTHER INFORMATION: Hybridoma producing human antibody 1-3-1

<400> SEQUENCE: 42
caatcagcag acagcagtgg tacttatgag gta                                   33
```

HUMAN MONOCLONAL ANTIBODY SPECIFICALLY BINDING TO SURFACE ANTIGEN OF CANCER CELL MEMBRANE

This is a divisional of application Ser. No. 08/360,125 filed Dec. 20, 1994, now patented (U.S. Pat. No. 5,767,246), which was a continuation of now abandoned application Ser. No. 07/905,534 filed Jun. 29, 1992.

BACKGROUND OF THE INVENTION

1. Field of the Invention

The present invention relates to a novel human monoclonal antibody useful for diagnosis and therapy of cancer, an isolated DNA encoding the monoclonal antibody, and a hybridoma producing the antibody. The present invention also relates to an anti-cancer formulation comprising the antibody bonded to a liposome which contains an anti-cancer agent.

2. Description of the Related Art

There has been no anti-cancer formulation thus far, which is sufficiently effective for the treatment of solid cancer. On the other hand, there has long existed an idea called "targeting" in which a therapeutical agent is concentrated at a tissue or an organ to be treated in order to maximize the therapeutical effect of the agent. Accordingly, it has been expected that focusing an anti-cancer agent at a cancer tissue by means of "targeting" may allow a therapy of the solid cancer. A number of trials to concentrate an anti-cancer agent or a toxin at a cancer tissue were made since a method for production of mouse monoclonal antibodies in large quantities has been established by Milstein and Köhler (Nature, 1975), and some of them were successful.

Thus far, binding of an antibody to a therapeutic agent has been accomplished by directly binding an antibody to a chemically-modified therapeutic agent, or indirectly binding them via a water-soluble polymer such as dextran. These methods, however, have drawbacks in that the amount of a therapeutic agent capable of binding to one antibody molecule is very limited, and in that chemical modification of a therapeutic agent often causes lowering of the therapeutical activity. As one of the countermeasures to overcome the drawbacks, there was proposed a new delivery system which consists of an antibody bonded to the surface of a liposome in which a therapeutic agent is encapsuled, and many favorable results were reported (Konno et al, Cancer Research 47 4471, 1987; Hashimoto et al, Japanese Patent Publication (unexamined) No. 134032/1983).

However, mouse monoclonal antibodies have a limited clinical use and continued administration thereof is impossible from a practical point of view due to side effects such as anaphylaxis caused by immune response (See A. Lo Bugli et al, Proc. Natl. Acad. Sci. U.S.A., 86 4220, 1989). Accordingly, human monoclonal antibodies rather than mouse monoclonal antibodies are preferable for the purpose of clinical use. However, preparation of human monoclonal antibodies which adequately react with cancer cells has long been considered very difficult because of the reasons that it is very difficult to conduct passive immunity for the purpose of obtaining human B cells which produce a desired antibody, and that any efficient methodology which allows infinite reproduction of antibody-producing cells has not been established yet.

In such a situation as mentioned above, the inventors of the present invention have made extensive study for the purpose of obtaining a human monoclonal antibody which permits "targeting therapy" on cancer tissue or organ with the help of anti-cancer agents or toxins, and they have succeeded in preparing a hybridoma capable of producing a novel human monoclonal antibody, the antigen to which exists on the surface of cell membrane of cancer cells. They also have succeeded in preparing a therapeutical formulation useful for "targeting therapy" of cancer, by binding the monoclonal antibody of the invention to a liposome in which an anti-cancer agent is encapsuled. The present invention is based on these findings.

Thus, the present invention provides a human monoclonal antibody specific to an antigen existing on the surface of a cancer cell membrane, said monoclonal antibody being produced by a fused cell between a lymphocyte derived from cancer patient and a mouse myeloma cell. The invention further provides an isolated gene encoding the antibody, a hybridoma producing the antibody, and an anti-cancer formulation containing the antibody.

SUMMARY OF THE INVENTION

The human monoclonal antibodies of the present invention contain, in the variable region of the heavy chain, the amino acid sequences shown, for instance, in Sequence Listing Nos. 13, 14, and 15. More specifically, the monoclonal antibodies of the invention include, among others, those in which the variable region of the heavy chain comprises the amino acid sequences shown in Sequence Listing Nos. 16, 17, and 18, and the variable region of the light chain comprises the amino acid sequences shown in Sequence Listing Nos. 19, 20, and 21, and those in which the variable region of the heavy chain comprises the amino acid sequences given in Sequence Listing Nos. 22, 23, and 24, and the variable region of the light chain comprises the amino acid sequences given in Sequence Listing Nos. 25, 26, and 27.

The monoclonal antibodies of the invention include any variants of the above-mentioned specific antibodies, which are obtainable by making insertion, deletion, substitution and/or addition of one or more amino acid residues to the amino acid sequences of the above-identified antibodies with the limitations that such modification must not adversely affect the reactivity of the antibodies against the antigens. The present invention will be addressed in more detailed below.

DESCRIPTION OF THE PREFERRED EMBODIMENTS

Figure 1:
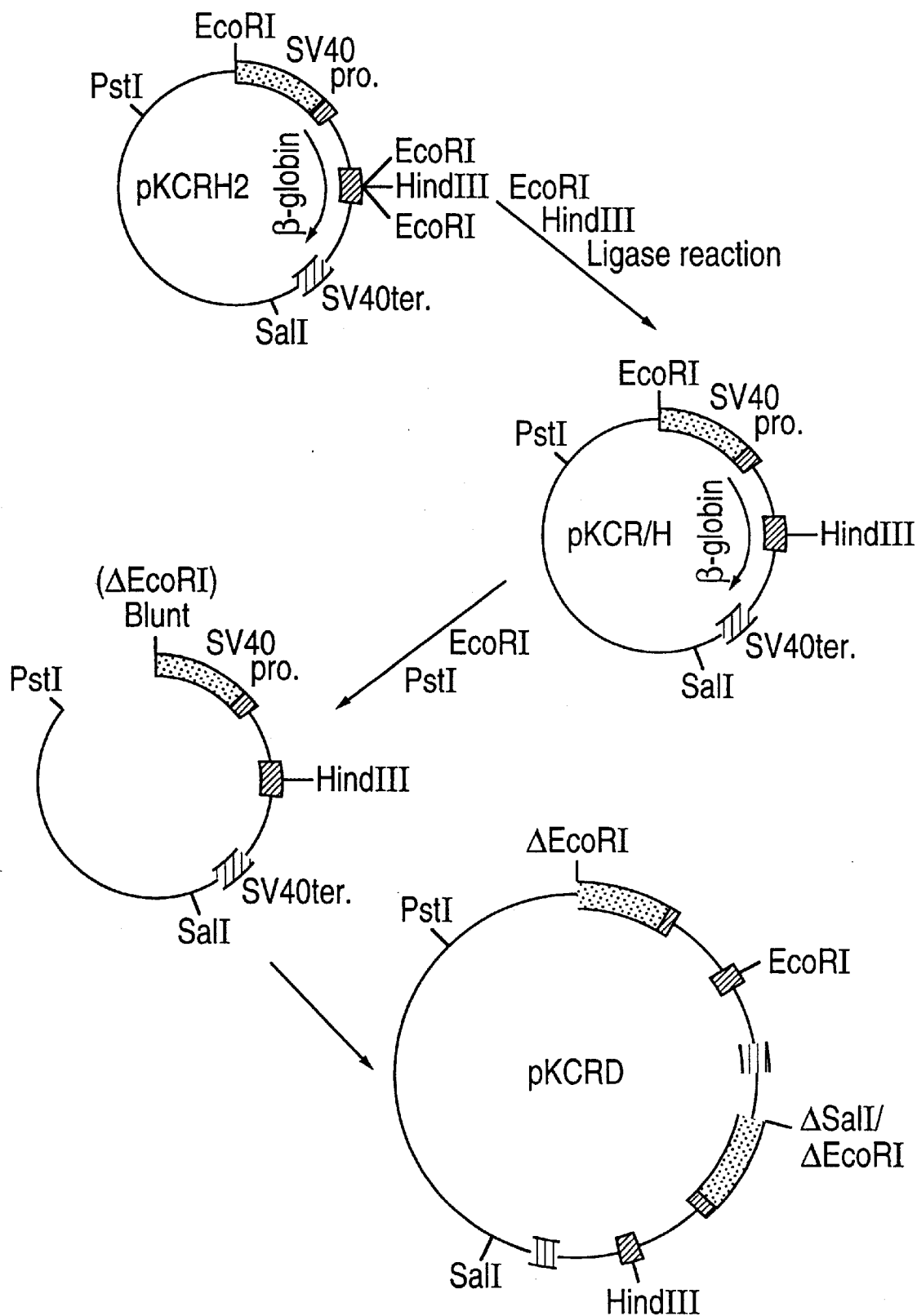
FIG. 1 schematically shows the construction of vector pKCRD.

The hybridoma producing a human monoclonal antibody of the invention is prepared according to the method described by A. Imam (Cancer Research 45 263, 1985). Thus, lymphocytes which have been isolated from extracted lymph node associated with cancer are fused with mouse myeloma cells in the presence of polyethylene glycol.

Hybridomas thus obtained are screened by means of enzyme immunoassay using various cancer cell line fixed with paraformaldehyde, and hybridomas capable of producing antibodies are obtained and cultured. From supernatant of the resulting culture, monoclonal antibodies are isolated and purified according to a conventional method such as disclosed by R. C. Duhamel (J. Immunol. Methods 31 211, 1979).

The purified monoclonal antibody is labelled with a fluorescent substance and examined about its reactivity with living cancer cells and normal cells such as erythrocytes and leucocytes using Flow Cytometry. Hybridoma producing an antibody which reacts with the living cells but not with normal cells are selected. Alternatively, the reactivity of antibodies to cancer cells isolated from cancer tissue of a patient is compared with the reactivity to normal cells derived from non-cancer segment of the same organ, and a hybridoma producing an antibody which reacts with the cancer cell and does not react, or reacts as moderately as an antibody derived from normal volunteer, with normal cells, is selected.

A base sequence of a DNA encoding a human monoclonal antibody produced by the hybridoma selected above can be determined in the following manner.

In accordance with Casara et al method (DNA 2 329, 1983), mRNAs are separated from the antibody-producing hybridoma cells, using guanidine thiocyanate-lithium chloride, and cDNA library is prepared by the use of oligo (dT) primer. The cDNAs thus obtained are then subjected to (dG) tailing. Consensus sequence between poly C capable of hybridizing with the dG tail obtained above and an already available human gene encoding heavy or light chain of human antibodies is used as a probe for amplification of the antibody-encoding CDNA by means of PCR. The terminal of the amplified DNA is made blunt. The DNA separated from an electrophoresis gel is inserted to a cloning vector such as pUC119, and the base sequence of the DNA is determined by Sanger et al dideoxy method (Proc. Natl. Acad. Sci. U.S.A. 74 5463, 1977).

Preferable antibodies of the present invention are those in which the variable region of the heavy chain comprises the amino acid sequences shown in Sequence Listing Nos. 13, 14, and 15. Specific examples of preferred antibodies are, among others, those in which the variable region of the heavy chain comprises the amino acid sequences shown in Sequence Listing Nos. 16, 17, and 18, and the variable region of the light chain comprises the amino acid sequences shown in Sequence Listing Nos. 19, 20, and 21, and those in which the variable region of the heavy chain comprises the amino acid sequences shown in Sequence Listing Nos. 22, 23, and 24, and the variable region of the light chain comprises the amino acid sequences shown in Sequence Listing Nos. 25, 26, and 27.

The above-noted amino acid sequences in Sequence Listing Nos. 13, 14, and 15; 16, 17, and 18; and 22, 23, and 24 are called "hyper variable region" in variable region of the heavy chain. Likewise, the amino acid sequences in Sequence Listing Nos. 19, 20, and 21; 25, 26, and 27 are called "hyper variable region" in variable region of the light chain. These regions are responsible for the specificity of the antibody and determinative to binding affinity between the antibody and the antigenic determinant. Accordingly, the variable region of the heavy chain in the antibodies of the invention can have various amino acid sequences derived from different antibodies so far as it comprises the above-mentioned hyper variable regions.

The most preferred monoclonal antibodies of the invention are those in which the variable regions of the heavy and light chains are represented by the amino acid sequences of Sequence Listing Nos. 5 and 6 respectively, and also 11 and 12 respectively. The DNA sequences encoding constant regions of the heavy and light chains are the same as those disclosed in Nucleic Acids Research 14 1779, 1986, The Journal of Biological Chemistry 257, 1516, 1982 and Cell 22, 197, 1980, respectively.

Figure 2:
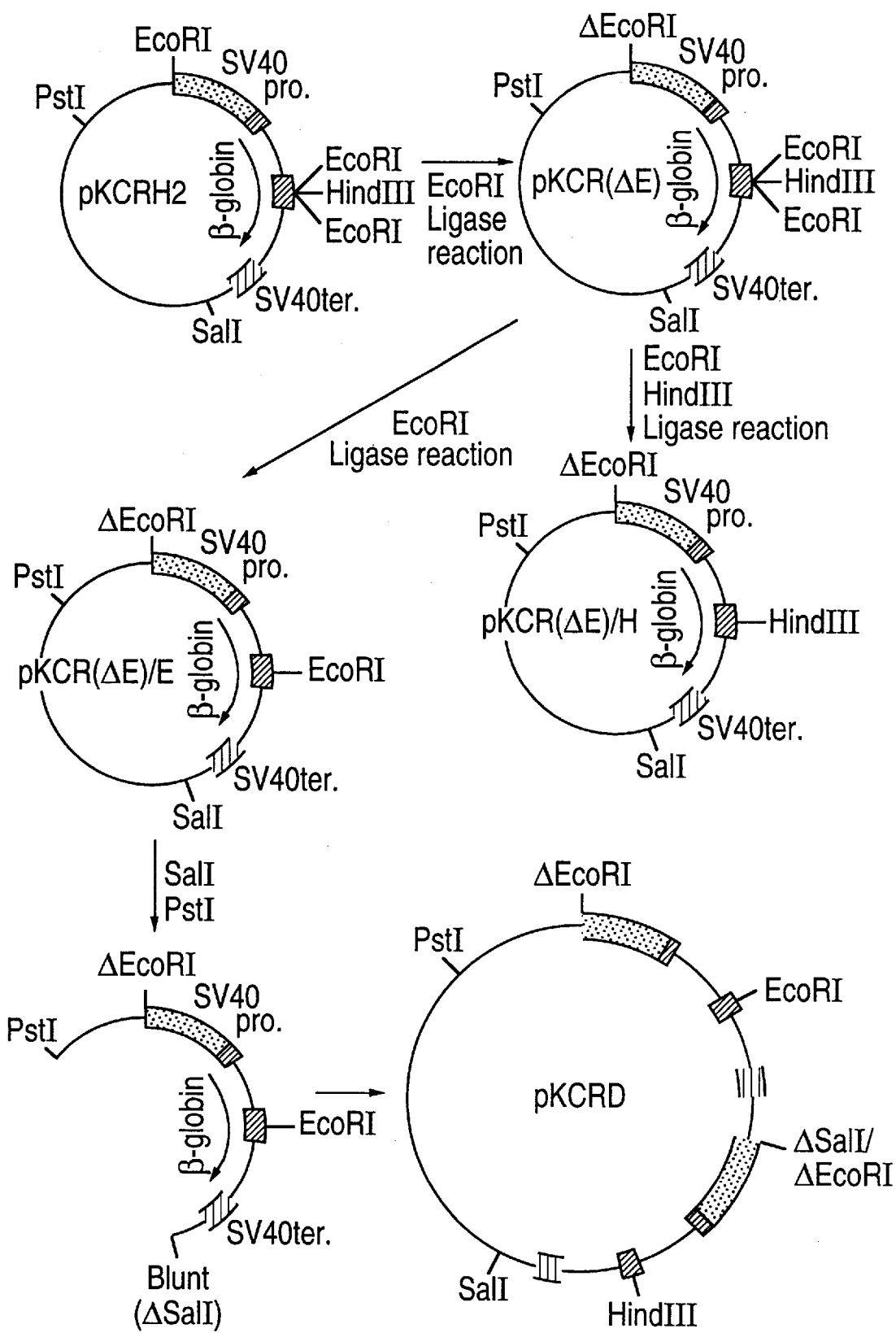
FIG. 2 schematically shows the construction of vector pKCR(ΔE)/H.

The monoclonal antibody of the invention may be prepared by culturing the hybridoma producing the antibody of the invention in eRDF or RPMI1640 medium containing fetal bovine serum. Alternatively, it may also be prepared by connecting the DNAs having the base sequences in Sequence Listing No. 3, 4, 9 and No. 10, which encode variable regions of heavy and light chains respectively, with known DNAs encoding the constant regions as mentioned above to obtain a pair of genes encoding the monoclonal antibody of the invention, inserting the genes into one of various known expression vectors, transforming an appropriate host cell such as CHO cell with the expression vectors, and culturing the resultant transformant. As expression vectors to be used in animal cells, there may conveniently used a combination of pKCR ($\Delta$E)/H and pKCRD which may be constructed in the manner as shown in FIGS. 1 and 2 starting from pKCRH2 disclosed by Mishina (Nature 307 605,1984). In more detail, a gene encoding the heavy chain, to which a HindIII restriction site has been added, is inserted into plasmid pKCR ($\Delta$E/H) at the HindIII site, and a selective marker such as DHFR gene is inserted into the plasmid at SalI site. On the other hand, a gene encoding the light chain, to both ends of which EcoRI restriction site has been added, is inserted into plasmid pKCRD at EcoRI site, and then the DHFR gene is also inserted into the plasmid at SalI site. Both of the plasmids obtained above are incorporated into a host cell such as CHO dhfr⁻ (Urlaub G. & Chasin L. A., Proc. Natl. Acad. Sci. U.S.A., 77 4216, 1980) by means of calcium phosphate method. The resultant transformant is cultured in $\alpha$MEM medium containing no nucleotide, and grown cells are subjected to further selection for antibody-producing clones. The antibody of the invention can be obtained and purified by culturing the selected clone, adsorbing the resulting supernatant to a column filled with Protein A supported by cerulofine or agarose, and eluting the antibody from the column.

A liposome used for the preparation of the anti-cancer formulation of the invention is composed of two lipid layers. The lipid layer may be of monolayer or multiple layers. Constituents of the liposome are phsphatidylcholine, cholesterol, phosphatidylethanolamine, etc. Phosphatidic acid, which provides the liposome with electric charge, may also be added. The amounts of these constituents used for the production of the liposome are, for instance, 0.3–1 mol, preferably 0.4–0.6 mol of cholesterol, 0.01–0.2 mol, preferably 0.02–0.1 mol of phosphatidylethanolamine, 0.0–0.4 mol, preferably 0–0.15 mol of phosphatidic acid per 1 mol of phosphatidylcholine.

The liposome used in the present invention may be prepared by conventional methods. For example, a mixture of the above-mentioned lipids, from which the solvents have been removed, is emulsified by the use of a homogenizer, lyophilized, and melted to obtain multilamera liposome. Adjustment of particle size of the resultant liposomes may be conducted by ultrasonication, high-speed homogenization, or pressure filtration through a membrane having uniform pore size (Hope M. J. et al., Biochimica et Biophysica Acta 812 55, 1985). Preferable particle size of the liposomes are between 30 nm and 200 nm.

Anti-cancer agents encapsuled in the liposome includes carcinostatic agents such as adriamycin, daunomycin, mitomycin, cisplatin, vincristine, epirubicin, methotrexate, 5Fu, and aclacinomycin, toxins such as ricin A and diphtheria toxin, and antisense RNA. Encapsulation of anti-cancer agent into liposome is accomplished by hydration of the lipids with an aqueous solution of the anti-cancer agent. Adriamycin, daunomycin, and epirubicin may be encapsulated into a liposome by means of remote loading method taking advantage of pH gradient (Lawrence D. M. et al., Cancer Research 49 5922, 1989).

Binding of a monoclonal antibody to the surface of the liposome mentioned above may be accomplished by the formation of cross-linkage between phosphatidylethanolamine and the antibody using glutaraldehyde. However, preferred method is that a thiolated antibody is allowed to react with a liposome comprising a lipid into which a maleimide group has been incorporated. Remaining maleimide groups on the surface of the liposome may be further reacted with a compound containing thiolated polyalkyleneglycol moiety, thereby the surface of the liposome is modified.

Thiolation of an antiobody may be conducted by the use of N-succinimidyl-3-(2-pyridyldithio)propionate (SPDP), which is usually used for thiolation of protein, iminothiolane, or mercaptoalkylimidate. Alternatively, a dithiol group intrinsic to an antibody may be reduced to form a thiol group. The latter is preferred from the view point of keeping antibody's function. Another method to provide an antibody with a thiol group is that an antibody is treated with an enzyme such as pepsin to form $F(ab)'_2$, which is then reduced with dithiothreitol (DTT) to form Fab', which gives one to three thiol groups.

The binding of the thiolated antibody to the maleimide group-containing liposome may be accomplished by reacting them in a neutral buffer solution at pH6.5–7.5 for 2–16 hours.

The anti-cancer formulation of the present invention may be prepared by means of conventional methods such as dehydration method (Japanese Patent Publication No. 502348/1990) and lyophilization method (Japanese Patent Publication No. 9331/1989).

The anti-cancer formulation of the invention may be administered intravascularly, peritoneally, or locally. Dosage of the formulation varies depending on the nature of particular anti-cancer agent encapsulated into the liposome. When the agent is adriamycin, the dosage is the one corresponding to adriamycin 50 mg or less/kg body weight, preferably 10 mg or less/kg, more preferably 5 mg or less/kg.

The following detailed examples are presented by way of illustration of certain specific embodiments of the present invention.

EXAMPLE 1

Establishment of Hybridoma Producing Human Monoclonal Antibody GAH

Hybridoma producing human monoclonal antibody GAH was established by cell fusion between lymphocytes derived from a lymph node associated with cancer tissue of a patient and mouse myeloma cells.

(1) Preparation of Lymphocytes

Cancer-associated lymph node extracted from a patient suffering from colon cancer was cut up into fine pieces with scissors and scalpel, and cells were dispersed using a stainless net in Culture Medium A (eRDF (Kyokuto Seiyaku Kogyo)+50 μg/ml gentamicin sulfate). The resultant cell suspension was centrifuged at 1000 rpm for 10 minutes and the supernatant was discarded. The residue was suspended in fresh Culture Medium A, and the suspension was centrifuged again to obtain $2.6 \times 10^7$ cells.

(2) Cell Fusion

The lymphocyte cells obtained above were subjected to cell fusion with mouse myeloma cells ($1 \times 10^7$) in the presence of polyethyleneglycol (Boehringer-Mannheim) according to a conventional method. The fused cells were suspended into Culture Medium A added with 10 μM hypoxanthine, 0.04 μM aminopterin, 1.6 μM thymidine, and 10% fetal calf serum (FCS), said medium being referred to as HAT addition medium hereinafter, so that the density of the lymphocytes may be $5.4 \times 10^5$/ml. The suspension was plated on 96 well plates at 100 μl/well and cultured at 37° C. in a $CO_2$ incubator. Half of the culture medium was substituted with HAT addition medium from time to time and the cultivation was continued until hybridoma's colonies appeared. The hybridoma's colonies were observed in all of the wells. The supernatant of the culture in each well was tested on the reactivity to several established cancer cell lines such as colon cancer cell line C-1 (Sato et al, Igakunoayumi (Progress of Medicine) 96 876, 1976, obtained from Men Eki Seibutsu Kenkyusho (Institute of Immunized Organisms)), and stomach cancer cell line MKN45 (Naito et al, Gan to Kagaku Ryoho (Cancer and Chemotherapy) 5 89, 1978, obtained from above-noted Institute) according to the method described in Experiment 1. Positive wells were 7.3% (35 wells) against C-1 and 4.6% (22 wells) against MKN45, and 6 wells showed positive reaction to both strains. Cloning of hybridomas was conducted using the wells which showed positive reaction to both lines. The cloning was conducted three times by means of limiting dilution method, and hybridoma clone GAH was established.

EXAMPLE 2

Purification and Labeling of Monoclonal Antibody GAH (1) Culture of Hybridoma GAH and Purification of Monoclonal Antibody GAH Fetal calf serum was passed through a Protein A-agarose (RepliGen), thereby substances adsorbed to the column was removed from the serum. For culture of hybridoma GAH, eRDF culture medium (Kyokuto Seiyaku) to which 3% of the above serum had been added was used. The culture of hybridoma GAH was then charged into a Protein A-agarose column, and adsorbed antibody was then eluted out to obtain purified antibody. The use of the above-noted serum allowed to obtain pure antibody GAH free from other antibodies of serum origin and substances adsorbed to Protein A-agarose. The antibody GAH was confirmed to be a pure IgG by sodium dodecyl sulfate-polyacrylamide gel electrophoresis.

(2) Fluorescent Labeling of Antibody GAH

The purified antibody GAH was labeled by fluorescein isothiocyanate (FITC) according to the method of Coons A. H. Thus, the antibody was dialyzed against a carbonate buffer solution (pH9.5) and reacted with FITC solution. The labeled antibody was separated from free FITC by gel filtration. Absorbance of fractions containing labeled antibody was measured at $OD_{280\ nm}$ and $OD_{495\ nm}$ and labeling degree was determined. The binding molar ratio of the antibody and FITC (F/P ratio) was 0.93.

Experiment 1

Study on Reactivity of Human Monoclonal Antibody against Cancer Cell Lines (1) Cancer Cell Lines and Preservation Thereof Colon cancer cell line C-1 and stomach cancer cell line MKN45 were used as human cancer cell lines. The cells were preserved and grown at 37° C. under 5% $CO_2$ conditions using Culture Medium B (eRDF medium containing 10% FCS).

(2) Study on Reactivity to Cancer Cell Lines a. Determination of Reactivity Against Solid Cancer Cell Lines Cancer cells were cultured until monolayer in a 96 well plate for 3 or 4 days. After removal of culture supernatant, the plate was washed twice by 10 mM phosphate buffer (pH7.4) and 0.15M NaCl solution (PBS), and 2% paraformaldehyde fixation was conducted at room temperature for 20 minutes. After washing 5 times with PBS, PBS solution containing 5% BSA (bovine serum albumin) was added to wells (200 μl/well), and the plate was kept 37° C. for 2 hours to complete blocking. The plate was washed 5 times with PBS, and 50 μl of culture supernatant of hybridoma was added thereto. After two hour reaction at 37° C., the plate was washed 5 times with PBS and 50 μl of alkaliphosphatase conjugated goat antibody to human antibody (1000 dilution, Capel) was added. Following one hour reaction at 37° C., the plate was washed 5 times with PBS and added with 0.05M carbonate buffer—1 mM MgCl (pH9.5) containing 25 mM p-nitrophenyl phosphate at ratio of 50 μl/well and allowed to react at room temperature for one hour to overnight. Absorbance at 405 nm was measured with micro-plate photometer (Colona). Reactivity was determined according to the method described in Example 1 (2). Cloning from the wells in which positive reaction against cultured cancer cell lines C-1 and MKN45 has been observed gave hybridoma GAH. Purified antibody from culture supernatant of GAH showed the same reactivity.

b. Reactivity to Living Cancer Cells

Cancer cells were cultured in a flask or Petri dish and culture supernatant was discarded. To the residue was added a PBS solution containing 0.02% EDTA, and the mixture was left to stand at room temperature for 30 minutes allowing the cells to float. The cells were washed with Culture Medium B by centrifugation and suspended in healthy human serum containing the fluorescent-labeled antibody GAH (final concentration: 50 μg/ml) obtained in Example 2 (2) so that cell density of about $1 \times 10^6/200$ μl may be obtained, and the suspension was allowed to react at 0° C. for 60 minutes. The suspension was centrifuged at 2000 rpm for 2 minutes and the supernatant was discarded. The remaining cells were suspended in 1 ml of PBS, washed by centrifugation, and resuspended in 300 μl of PBS containing 10 μg/ml of propidium iodide (PI). The suspension was subjected to the observation by flow cytometer (FCM), FACS440 (Becton Dickinson), in order to determine the magnitude of fluorescence (FITC and PI) bonded to particular cell. Dead cells having PI fluorescence could be removed because the dead cells took in PI in the nucleic acids and emitted PI fluorescence. Markers having five standard amounts of fluorescence (quantitative kit: Ortho Diagnostic Systems) were subjected to FCM under the same conditioned as above. Based on the markers, average binding amount of FITC per cell was calculated. On the basis of the average binding amount and F/P ratio of labeled antibody, an average number of antibodies bonded to one living cell was determined. The results are shown in Table 1.

TABLE 1

| Cancer Cell Strain | Antibody | |
|---|---|---|
| | GAH | Control IgG |
| MKN45 | $3.5 \times 10^4$ | $0.15 \times 10^4$ |
| C-1 | $0.6 \times 10^4$ | $<0.1 \times 10^4$ |

When compared with IgG derived from healthy human serum, which was labeled by fluorescence in the same manner as GAH and used as a control, about 6–23 times larger amount of antibody GAH has bonded to stomach and colon cancer cells.

Experiment 2

Reactivity of Human Monoclonal Antibody GAH to Blood Cells

Erythrocytes were separated from peripheral blood taken from 7 healthy volunteers and 3 patients suffering from cancer according to Kinoshita's method (Separation of Erythrocytes; New Edition of Nippon Ketsuekigaku Zensho 13 800, 1979).

Leukocytes were obtained in the following manner: Peripheral blood was drawn from healthy volunteers with addition of heparin. 2 ml of 6% dextran-physiological saline was added and mixed to 10 ml of the blood. The mixture was left to stand at room temperature for 50 minutes to give a plasma layer, which was then separated and centrifuged at 1500 rpm for 5 minutes to obtain leukocytes.

Reactivities of the monoclonal antibody of the invention to these blood cells were determined by means of FCM in the same manner as in the living cancer cells except that PI was not added. In this connection, the leukocytes were divided into lymphocyte (major leukocyte cell), granulocyte, monocyte, and platelet, based on front and side light scattering in FCM (Bio/Technology 3 337, 1985), and reactivities to respective cells were separately determined. The test results were shown in Table 2.

TABLE 2

| Cells | Antibody | |
|---|---|---|
| | GAH | Control IgG |
| Leukocyte | | |
| lymphocyte | negative | negative |
| granulocyte | $0.49 \times 10^{4*}$ | $0.48 \times 10^{4*}$ |
| monocyte | $0.41 \times 10^{4*}$ | $0.43 \times 10^{4*}$ |
| platelet | negative | negative |
| Erythrocyte | negative | negative |

*: Average number of antibodies bonded per cell

Antibody GAH showed no reaction to erythrocyte and lymphocyte, while the reactivity to granulocyte and monocyte was the same level as the reactivity to control IgG likewise in Experiment 1.

Experiment 3

Reactivity of Human Monoclonal Antibody GAH to Cells Derived from Fresh Cancer Tissue and Non-Cancer Tissue In order to study a binding specificity of antibody GAH to cancer cells, normal cells were simultaneously isolated from fresh tissue belonging to the same organ of the same patient from which cancer cells were obtained, and reactivities of antibody GAH to respective cells were determined. Isolation of cells from the tissue was conducted according to Tokita's method (Ganno Rinsho (Cancer in Clinic) 32 1803,1986).

Thus, the tissue extracted was placed on Teflon sheet spreaded on a rubber plate, cut with a razor into fine pieces, and transferred onto a 1 mm stainless meshes. The meshes was shaken in a Petri dish full of a culture medium to obtain the medium containing small cell aggregates which passed through the meshes. The medium was centrifuged at 1000 rpm, and floating fats and suspending necrotic debris were discarded. This centrifugation was repeated several times. The cell aggregates were subjected to pumping by means of a syringe with Cateran needle of 23 gauge to disperse the cells. The reactivity to the cells thus obtained was determined by FCM in the same manner as in the living cancer cells. The test results are shown in Table 3.

TABLE 3

| Antibody | Colon | | Stomach | |
| --- | --- | --- | --- | --- |
| | Cancer Cells | Non-cancer Cells | Cancer Cells | Non-cancer Cells |
| GAH | $1.1 \times 10^4$ | $0.03 \times 10^4$ | $180 \times 10^4$ | $4.6 \times 10^4$ |
| Control IgG | $0.15 \times 10^4$ | $0.04 \times 10^4$ | $3.5 \times 10^4$ | $0.9 \times 10^4$ |

Average Number of Antibodies Bonded Per Cell

The average number of GAH antibodies bonded to cancer cells is remarkably higher than that in the non-cancer cells. In addition, the number of antibodies bonded to cancer cells was 51 times greater than that in the control IgG in stomach cancer, and 7 times greater in colon cancer. These results indicate that antibody GAH recognizes an antigen dominantly expressed on the surface of cell membrane of cancer cells.

EXAMPLE 3

(1) Determination of Subclass of Light Chain of Monoclonal Antibody GAH

Antibody GAH obtained in Example 2 (1) was subjected to SDS-PAGE in the reduced form. Heavy chain and light chain separately electrophorated were blotted on a transmembrane (Polyvinylidene-dilluoride, Millipore). The membrane was blocked with 5% BSA solution and allowed to react with a goat antibody to human κ or λ chain, which was combined with peroxidase (Capel). After washing, a 0.05% (w/v) 4-chloronaphthol solution containing 0.015% $H_2O_2$ was allowed to react thereto as a substrate. The light chain of antibody GAH reacted with anti-human κ chain antibody, which was detected through the appearance of colored band. This revealed that the light chain was κ chain.

(2) Preparation of Gene Encoding Monoclonal Antibody GAH a. Preparation of cDNA Encoding Antibody GAH by Means of Polymerase Chain Reaction (PCR)

According to the method detailed below, poly(A)-containing RNAs were prepared from antibody GAH-producing hybridoma obtained in Example 1 (2) using guanidine thiocyanate-lithium chloride method (DNA 2 329, 1983).

The hybridoma cells ($1 \times 10^7$) were solubilized in a solution (7.5 ml) comprising 5M guanidine thiocyanate, 10 mM EDTA, 50 mM Tris-HCl, pH7.0, and 8% (v/v) β-mercaptoethanol. To the mixture was further added and mixed cesium chloride to the final concentration of 1 g/2.5 ml. The solution (8.0 ml) was gently overlayed on a 5.7M cesium chloride solution (3.5 ml) in a centrifuge tube, and centrifuged at 30,000 rpm for 23.5 hours using Hitachi RPS40T Rotary, which gave RNAs as a precipitate. The precipitate was dissolved in a solution (400 μl) comprising 0.1% sodium lauryl sulfate, 1 mM EDTA, and 10 mM Tris-HCl, pH7.5, followed by phenol-chloroform extraction and ethanol precipitation. The resultant RNAs (about 64 μg) was dissolved in a solution (40 μl) comprising 10 mM Tris-HCl, pH8.0, and 1 mM EDTA. A 21 μl aliquot of the solution provided about 2.64 μg of mRNA containing poly (A) by means of mRNA PURIFICATION KIT (Pharmacia). The poly(A)-containing mRNA (1.1 μg) was dissolved in water (10 μl). To the solution were added oligo d(T) 12–18 primer (1.5 μg) (Pharmacia), 10 mM 4 dNTP (3 μl) (Takara Shuzo), reverse transcriptase (40U) (Life Science), RNase inhibitor (30U) (Takara Shuzo), 5×reverse transcriptase buffer (6 μl) comprising 250 mM Tris-HCl, pH8.3, 40 mM magnesium chloride, and 250 mM potassium chloride, and additionally water to make a total volume of 30 μl. The mixture was allowed to react at 41° C. for one hour, followed by ethanol precipitation to obtain CDNA.

The CDNA thus obtained was dissolved in water (15.3 μl). To the solution were added a 5×terminal deoxynucleotide transferase buffer (4.8 μl) (250 mM Tris-HCl, pH7.5, 50 mM magnesium chloride), terminal deoxynucleotide transferase (12U) (Pharmacia), and 10 mM dGTP (2.4 μl) (Takara Shuzo) to make a total volume of 24 μl, and the mixture was allowed to react at 37° C. for 1.5 hours to add poly d(G) at 3' terminal of CDNA. After completion of the reaction, the enzymes were inactivated by heating at 70° C. for 15 minutes.

PCR was conducted based on the cDNA thus obtained as a template using Perkin Elmer Cetus DNA THERMAL CYCLER following the manual provided by the manufacturer. Thus, to the above reaction mixture (2 μl) were added, as a primer for amplifying cDNA encoding variable region of the heavy chain, poly C (15 nucleotides) which hybridizes dG tail added to 3' terminal of the cDNA (40 pmol), a single stranded DNA primer (37 nucleotides) corresponding to the region spanning from part of the variable region (113–119 amino acid sequence in Sequence Listing No. 5) to the constant region which is common to all human IgGs (25 pmol) (Nucleic Acids Research 14 1779, 1986), poly C as a primer for amplifying cDNA encoding variable region of the light chain (40 pmol), a single stranded DNA primer (21 nucleotides) corresponding to the region spanning from J region of human κ chain (113–114 amino acid sequence of Sequence Listing No. 6) to the constant region (The Journal of Biological Chemistry 257 1516, 1982; Cell 22 197, 1980) (40 pmol), 10×PCR buffer (100 mM Tris-HCl, pH8.3, 500 mM potassium chloride, 15 mM magnesium chloride, 0.1% (w/v) gelatin (10 μl), 10 mM 4 dNTP (2 μl) (Takara Shuzo), and Taq DNA polymerase (2.5U) (Takara Shuzo)), and further water to make a final volume of 100 μl. Thirty cycles of incubations at 94° C. for one minute (denaturing step) at 55° C. for two minutes (annealing step) and at 72° C. for three minutes (elongation step) were conducted and further incubation at 72° C. for seven minutes was added. Reaction mixture was subjected to ethanol precipitation, and resultant precipitates were dissolved in water (30 μl).

To the aqueous solution were added Klenow fragment (2U) (Takara Shuzo), 1 mM 4 dNTP (4 μl), and 10×blunting buffer (500 mM Tris-HCl, pH7.6, 100 mM magnesium chloride) (4 μl), 40 μl in total, and the mixture was allowed to react at 37° C. for 30 minutes to obtain a double-stranded CDNA having blunt ends.

b. Determination of Base Sequence of cDNA

The cDNA solution obtained above was subjected to 2% agarose electrophoresis, and a band was observed at about 500 bp. The band was cut away from the agarose gel. The CDNA was inserted into a cloning vector pUC119 at SmaI site, and the base sequence was determined by dideoxy method, which revealed that among total base sequence of the PCR fragment, the base sequences encoding variable regions of the heavy and light chains were respectively those shown in Sequence Listing Nos. 3 and 4.

The amino acid sequences of variable regions of heavy and light chains of antibody GAH produced by the above-mentioned hybridoma were deduced from the base sequences determined above and are respectively shown in Sequence Listing Nos. 5 and 6. Based on the base sequences determined, antibody GAH was shown to belong to IgG1 subclass. The DNA fragment, the base sequence of which has been determined, can be prepared by means of DNA synthesizer with good reproducibility, and therefore, the acquisition of the DNA fragment does not require the repetition of the above procedure.

EXAMPLE 4

Establishment of Human Monoclonal Antibody 1-3-1 Producing Hybridoma by Cell Fusion between Lymphocyte Derived from Cancer Associated Lymph Node and Mouse Myeloma (1) Preparation of Lymphocyte In substantial accordance with the procedure described in Example 1 (1), lymphocytes ($3\times10^7$) were prepared starting from cancer associated lymph node extracted from a patient with lung cancer.

(2) Cell Fusion

Lymphocyte cells obtained above were fused with mouse myeloma cells ($8\times10^6$) using polyethyleneglycol (Boehringer-Mannheim) according to the conventional method. In the same manner as Example 1 (2), the fused cells were suspended in HAT addition medium to obtain cell density of $5.2\times10^5$/ml and placed on a 96 well plate at a ratio of 100 μl/plate. Half of the culture medium was substituted with HAT addition medium from time to time and the culture was continued until hybridoma's colonies appeared. The hybridoma's colonies were observed in all of the wells. In the same manner as in Example 1 (2), the supernatant of the culture in each well was tested on the reactivity to fixed cancer cell lines such as colon cancer cell line C-1 and stomach cancer cell line MKN45, in accordance with the procedure described in Experiment 1 (2)-a. Positive wells were 16.3% (94 well) against C-1 and 6.3% (36 wells) against MKN45, and 4 wells showed positive reaction to both lines.

Cloning of hybridoma cells was conducted using the wells which showed positive reaction to both lines. The cloning was conducted three times by means of limiting dilution method, and hybridoma clone 1-3-1 was established.

EXAMPLE 5

Purification and Labeling of Monoclonal Antibody 1-3-1

(1) Culture of Hybridoma 1-3-1 and Purification of Monoclonal Antibody 1-3-1

For culture of hybridoma 1-3-1, eRDF culture medium (Gokuto Seiyaku) to which 3% of the serum described in Example 2 (1) had been added was used. The culture of hybridoma 1-3-1 was then charged into a Protein A-agarose column, and adsorbed antibody was then eluted out to obtain purified antibody 1-3-1. The antibody was confirmed to be a pure IgM by SDS-PAGE.

(2) Fluorescent Labeling of Antibody 1-3-1

The purified antibody 1-3-1 was labeled by FITC according to the method described in Example 2 (2). Absorbance of fractions containing labeled antibody was measured at $OD_{280\,n\eta}$ and $OD_{495\,nm}$, and labeling degree was determined. F/P ratio was 6.7.

Experiment 4

Study on Reactivity of Human Monoclonal Antibody to Cancer Cell Lines (1) Cancer Cell Lines and Preservation thereof Human colon cancer cell line C-1 and stomach cancer cell line MKN45 were preserved and grown at 37° C. and 5% $CO_2$ conditions in Culture Medium B in the same manner as described in Experiment 1 (1).

(2) Study on Reactivity to Living Cancer Cell Lines

Figure 3:
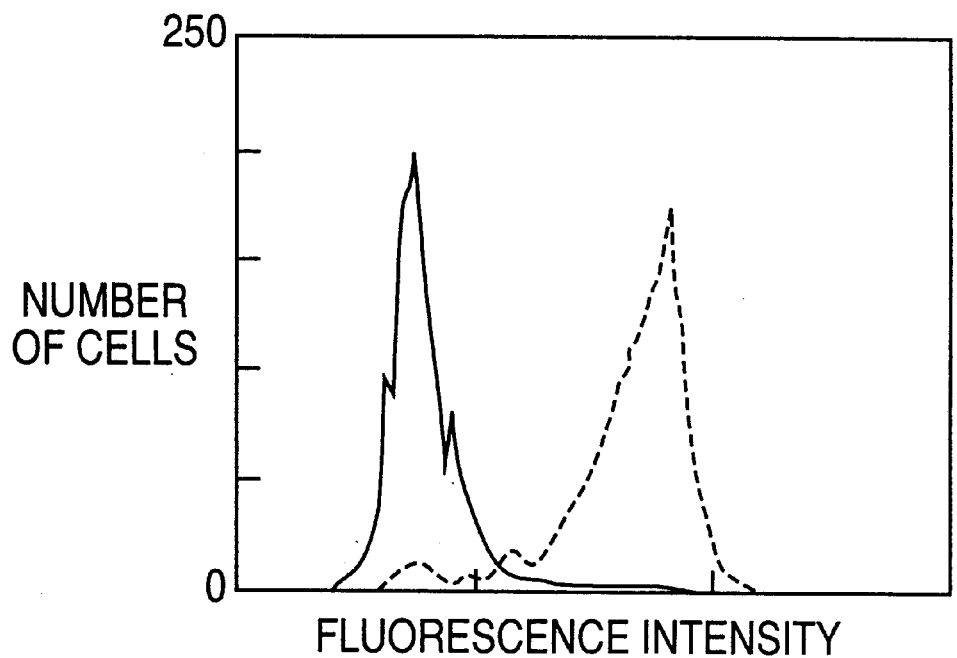
FIG. 3 shows reactivity of antibody 1-3-1 to colon cancer cell line C-1.
Figure 4:
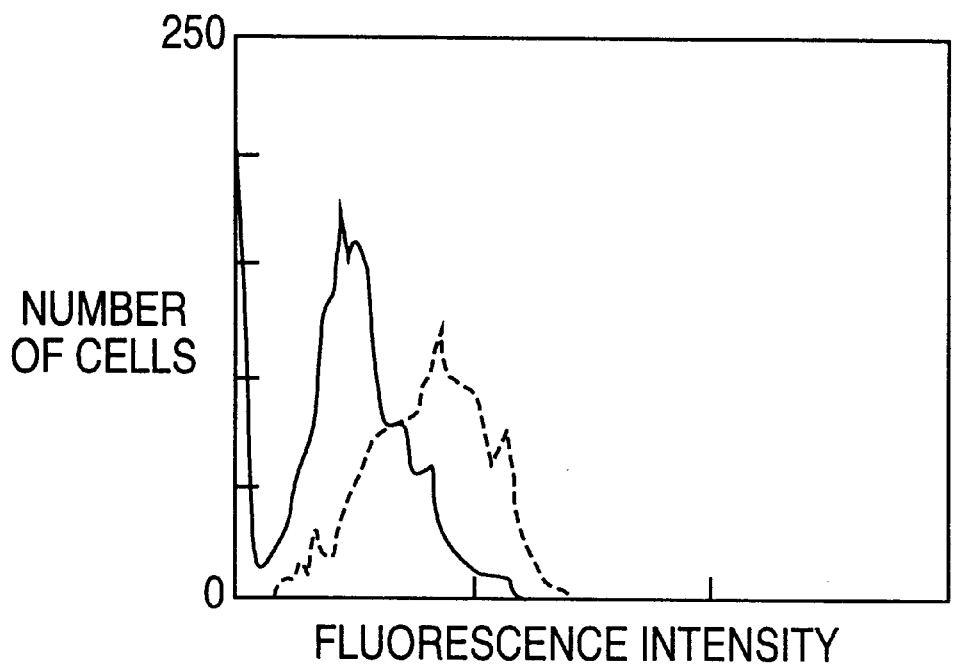
FIG. 4 shows reactivity of antibody 1-3-1 to gastric cancer cell line MKN45.

Cancer cells were cultured in a flask or Petri dish and culture supernatant was discarded. To the residue was added PBS solution containing 0.02% EDTA, and the mixture was left to stand at room temperature for 30 minutes allowing the cells to float. The cells were washed with Culture Medium B by centrifugation and suspended in PBS so as to make the cell density of about $1\times10^6$/200 μl. Antibody 1-3-1 obtained in Example 5 (1) was added to the above solution to make the final concentration of the antibody of 50 μg/ml, and the mixture was allowed to react at 0° C. for 60 minutes. The suspension was centrifuged at 2000 rpm for 2 minutes and the supernatant was discarded. To the remaining cells was added FITC labeled anti-human antibody solution (200 μl) (Capel) diluted with 1% BSA-containing PBS by 500 times, and the resulting cell suspension was kept at 0° C. for 60 minutes. The suspension was centrifuged at 2000 rpm for 2 minutes to remove the supernatant, and the remaining cells was suspended in and washed with PBS (1 ml) by centrifugation, and the cells were finally suspended in PBS (300 μl) containing PI (10 μg/ml). The resultant cell suspension was subjected to FCM, and magnitude of fluorescence (FITC and PI) bonded to particular cell was determined. The reactivities of antibody 1-3-1 to colon cancer cell line C-1 and stomach cancer cell line MKN45 are respectively shown in FIGS. 3 and 4 of the accompanying drawings. In the figures, the abscissa shows fluorescence intensity per cancer cell and the ordinate shows the number of the cancer cells. As a control, a commercially available IgM antibody (Capel) was used, and the reactivities of the IgM antibody to the above-identified cancer cells were determined. In the figures, the dotted line and solid line show the reactivities of antibody 1-3-1 and the control respectively. These figures show that antibody 1-3-1 has a strong binding ability to cancer cells.

Experiment 5

Reactivity of Human Monoclonal Antibody 1-3-1 to Cells Derived from Fresh Cancer Tissue and Non-Cancer Tissue In order to study a binding specificity of antibody 1-3-1 to cancer cells, normal cells were simultaneously isolated from fresh tissue belonging to the same organ of the same patient, from which cancer cells were obtained, and reactivities of antibody 1-3-1 to respective cells were measured. Isolation of cells from the tissue was conducted according to Tokita's method as described in Experiment 3.

The reactivity to the cells obtained above was determined by FCM in the same manner as previously described in the living cancer cells. However, the cells were washed with Culture Medium B, suspended in serum derived from healthy volunteers, which serum contained fluorescent labeled antibody 1-3-1 (final concentration of 50 μg/ml) prepared in Example 5 (2), to the cell density of about 1×10⁶/200 μl. The suspension was allowed to react at 0° C. for 60 minutes and subjected to centrifugation at 2000 rpm for 2 minutes to remove the supernatant. The remaining cells were suspended in PBS (1 ml) and washed by centrifugation. The cells were resuspended in PBS (300 μl) containing PI (10 μg/ml), and the suspension was subjected to FCM. The amount of fluorescent (FITC and PI) bonded to a particular cell was measured. Markers (5 species) for determining the amount of fluorescence (quantitative kit as previously prescribed) were subjected to FCM under the same condition. Average amount of FITC bonded to a single cell was calculated. Based on the average amount and F/P ratio of labeled antibody calculated in Example 5 (2), the average number of antibodies bonded to a living cancer cell was calculated. The results are shown in Table 4.

TABLE 4

| Antibody | Colon | | Stomach | |
| --- | --- | --- | --- | --- |
| | Cancer Cells | Non-cancer Cells | Cancer Cells | Non-cancer Cells |
| 1-3-1 | 1.5 × 10⁴ | 0.04 × 10⁴ | 1.8 × 10³ | 0.05 × 10³ |
| Control | 0.15 × 10⁴ | 0.04 × 10⁴ | 0.2 × 10³ | 0.3 × 10³ |

The reactivity of the human monoclonal antibody 1-3-1 to non-cancer cells was the same level as, or less than, that of the antibody which was derived from peripheral blood of healthy volunteers and fluorescent-labeled in the same manner as antibody 1-3-1, while the average number of antibodies bonded to cancer cells is remarkably higher than that in the non-cancer cells. In addition, the number of antibodies bonded to cancer cells was 10 times greater than that in the control antibody both in stomach and colon cancer. These results indicate that antibody 1-3-1 recognizes an antigen dominantly expressed on the surface of cell membrane of cancer cells.

EXAMPLE 6

(1) Determination of Subclass of Light Chain of Monoclonal Antibody 1-3-1

In order to determine the subclass of the light chain of antibody 1-3-1, the same procedure as described in Example 3 was repeated except that antibody 1-3-1 obtained in Example 5 (1) was used in place of antibody GAH. The light chain of antibody 1-3-1 reacted with anti-human λ chain antibody, which was detected through the appearance of coloured band. This revealed that the light chain was λ chain.

(2) Preparation of Gene Encoding Monoclonal Antibody 1-3-1 and Determination of Base Sequence a. Preparation of cDNA Encoding Antibody 1-3-1 by Means of PCR According to the method detailed below, poly(A) containing RNAs were prepared from antibody 1-3-1 producing hybridoma obtained in Example 4 (2) using guanidine thiocyanate-lithium chloride method (DNA 2 329, 1983).

In the same manner as described in Example 3 except that the number of hybridoma cells used was 2×10⁸, the mRNA was prepared. The resultant RNAs (about 1.8 mg) was dissolved in a solution (1 ml) comprising 10 mM Tris-HCl, pH8.0, and 1 mM EDTA. A 230 μl aliquot of the solution provided about 20 μg of mRNA containing poly(A) after purification by means of mRNA PURIFICATION KIT (Pharmacia). Following the procedure described in Example 3, the poly(A)-containing mRNA (4.3 μg) was dissolved in water (10 μl), and to the solution were added oligo d(T) 12–18 primer (0.6 μg), 10 mM 4 dNTP (2 μl), reverse transcriptase (40U), RNase inhibitor (30U), 5×reverse transcriptase buffer (6 μl), and additionally water to make a total volume of 30 μl. The mixture was allowed to react at 42° C. for one hour, followed by ethanol precipitation to obtain CDNA.

The cDNA thus obtained was dissolved in water (20 μl). To the solution were added a 5×terminal deoxynucleotide transferase buffer (5 μl), terminal deoxynucleotide transferase (11U), and 10 mM dGTP (2.5 μl) to make a total volume of 25 μl by adding water (6.5 μl), and the mixture was allowed to react at 37° C. for 1 hour to add poly d(G) at 3' terminal of cDNA. After completion of the reaction, the enzymes were inactivated by heating at 70° C. for 10 minutes.

PCR was conducted using the cDNA thus obtained as a template. Thus, to the above reaction mixture (2.5 μl) were added, as a primer for amplifying cDNA encoding variable region of the heavy chain, poly C (14 nucleotides) which hybridizes dG tail added to 3' terminal of the cDNA (25 pmol), a single stranded DNA primer (17 nucleotides) corresponding to the base sequence of constant region of IgM shown in Sequence Listing No. 7 (25 pmol) (Nucleic Acids Research 18 4278, 1990), poly C as a primer for amplifying cDNA encoding variable region of the light chain (25 pmol), a single stranded DNA primer (19 nucleotides) (25 pmol) corresponding to the base sequence of constant region of λ chain, shown in Sequence Listing No. 8 (Nature 294 536, 1981). The mixture was treated in the same manner as described in Example 3, which provided a double-stranded cDNA having blunt ends.

b. Determination of Base Sequence of cDNA

The cDNA solution obtained above was subjected to 2% agarose electrophoresis, and a band was observed at about 500 bp. The band was cut away from the agarose gel. The cDNA was inserted into a cloning vector pUC119 at SmaI site, and the base sequence was determined by dideoxy method, which revealed that among total base sequence of the PCR fragment, the base sequence encoding variable regions of the heavy and light chains were respectively those shown in Sequence Listing Nos. 9 and 10.

The amino acid sequences of variable regions of heavy and light chains of antibody 1-3-1 produced by the above-mentioned hybridoma were deduced from the base sequences determined above and are respectively shown in Sequence Listing Nos. 11 and 12. The DNA fragment, the base sequence of which has been determined, can be prepared by means of DNA synthesizer with good reproducibility, and therefore, the acquisition of the DNA fragment does not require the repetition of the above procedure.

EXAMPLE 7

Preparation of Adriamycin-Containing Liposome Bonded to Antibody GAH a. Preparation of Thiolated Antibody Anti-cancer antibody GAH (IgG) was dissolved in 0.1M—acetate buffer (pH4.0), and pepsin (1/40 mol) (Cooper Biomedical) was added thereto. The mixture was allowed to react overnight to prepare F(ab')$_2$. Chromatography over cation-exchange resin (mono S) (Pharmacia) isolated F(ab')$_2$. The solvent used was a linear gradient of 0.1M—acetate buffer (pH4.0) containing 0–0.5M NaCl. To the isolated F(ab')$_2$ in 0.1M—acetate buffer (pH4.5) containing 0.15M NaCl was added DTT at a ratio of 12$\mu$l of 10% DTT/1mg antibody. The mixture was left to stand at room temperature for 80 minutes. After completion of reaction, the mixture was passed through a gel filtration column (PD-10) equilibrated with PBS for desalification to obtain thiolated Fab'.

b. Thiolation of polyethylene/glycol

L-cysteine (48 mg) was dissolved in 0.4M borate buffer (10 ml), and 2,4-bis (polyethylene glycol)-6-chloro-s-triazine (200 mg) (activated PEG 2) (Seikagaku Kogyo) was added thereto. The mixture was allowed to react at room temperature overnight. To the resultant PEG bonded with cysteine was added DTT (62 mg), and the mixture was allowed to react at 37° C. for 6 hours to obtain a solution containing PEG bonded with cysteine. The solution was gel filtrated (GH-25, Seikagaku Kogyo) for desalting, and the solvent was substituted by 10 mM phosphate buffer (pH7.4) and 0.15M-NaCl (PBS). The solution was added to thiopropyl Sepharose 6B (Pharmacia) equilibrated with PBS, and non-bonded substances were washed away by PBS. Cysteine-binding PEG adsorbed to the gel was eluted out by PBS containing 50 mM-DTT, which was then subjected to gel filtration to remove excessive DTT. This gave thiolated PEG.

c. Maleimidation of dipalmitoylphosphatidylethanolamine

Dipalmitoylphosphatidylethanolamine (127 mg), N-($\epsilon$-maleimidecaproyloxy)succinimide (EMCS) (80 mg), and triethylamine were added to a chloroform/methanol (5:1) solution (44 $\mu$l), and the mixture was allowed to react for 3 hours under nitrogen gas. Additional EMCS (20 mg) was added and the mixture was allowed to react at room temperature for further 3 hours. After confirmation of negative ninhydrin reaction of the reaction mixture, the mixture was evaporated to dryness under reduced pressure and the residue was dissolved in a trace amount of chloroform. The maleimidated dipalmitoylphosphatidylethanolamine thus obtained was purified by chromatography over UNISIL (Gasukuro Kogyo) equilibrated with chloroform, using a chloroform/methanol (10:1) solution as an eluent.

d. Preparation of Liposome Containing Adriamycin Bearing Maleimide Group

Solid lipid mixture (100 mg) (Nippon Seika), which consists of dipalmitoylphosphatidylcholine (DPPC), cholesterol (Chol), and maleimidated dipalmitoylphosphatidylethanolamine at a ratio of 18:10:0.5 (mol) was added to 0.3M citrate buffer (pH4) (1 ml) and admixed. Freezing and thawing of the mixture was repeated 5 times to achieve hydration. This gave multimera liposome. The liposome was charged in an extruder (Lipex×Biomembranes) equipped with a polycarbonate membrane (Nucleopore; Microscience) having a pore size of 200 nm and kept at 60° C. Repeated pressure-filtration (10 times) gave a dressed liposome. The liposome solution was neutralized with addition of 1M NaOH solution, and to the neutral solution was added one tenth (by weight) of adriamycin (Kyowa Hakko) with respect to the lipid components while being kept at 60° C. More than 97% of adriamycin was positively enclosed into the liposome according to the pH slope between the inside and outside of the liposome to give a liposome into which adriamycin bearing maleimide group had been encapsulated.

e. Binding of Maleimide Group-bearing Adriamycin-encapsulated Liposome to Thiolated Antibody and PEG Modification To the adriamycin-encapsulated liposome obtained above (lipid components: 100 mg) was added thiolated Fab' antibody (5 mg), and the mixture was allowed to react at 37° C. for 8 hours. To the reaction mixture was added thiolated PEG (5 $\mu$mol), and the mixture was allowed to react in PBS at room temperature for 6 hours to obtain adriamycin-encapsulated liposome bonded to antibody and modified with PEG. The latter was further subjected to gel filtration using SEPHAROSE C16B (Pharmacia) to remove non-reacted cysteine-binding PEG.

Experiment 6

Confirmation of Pharmaceutical Effectiveness of Adriamycin-Encapsulated Liposome Bonded to Antibody GAH and Modified with PEG Study on anti-cancer effect of antibody GAH was conducted in the manner as described below using human stomach cancer cell line MKN45 which had shown reactivity to antibody GAH and accumulative behavior in transplantation to nude mouse.

Figure 5:
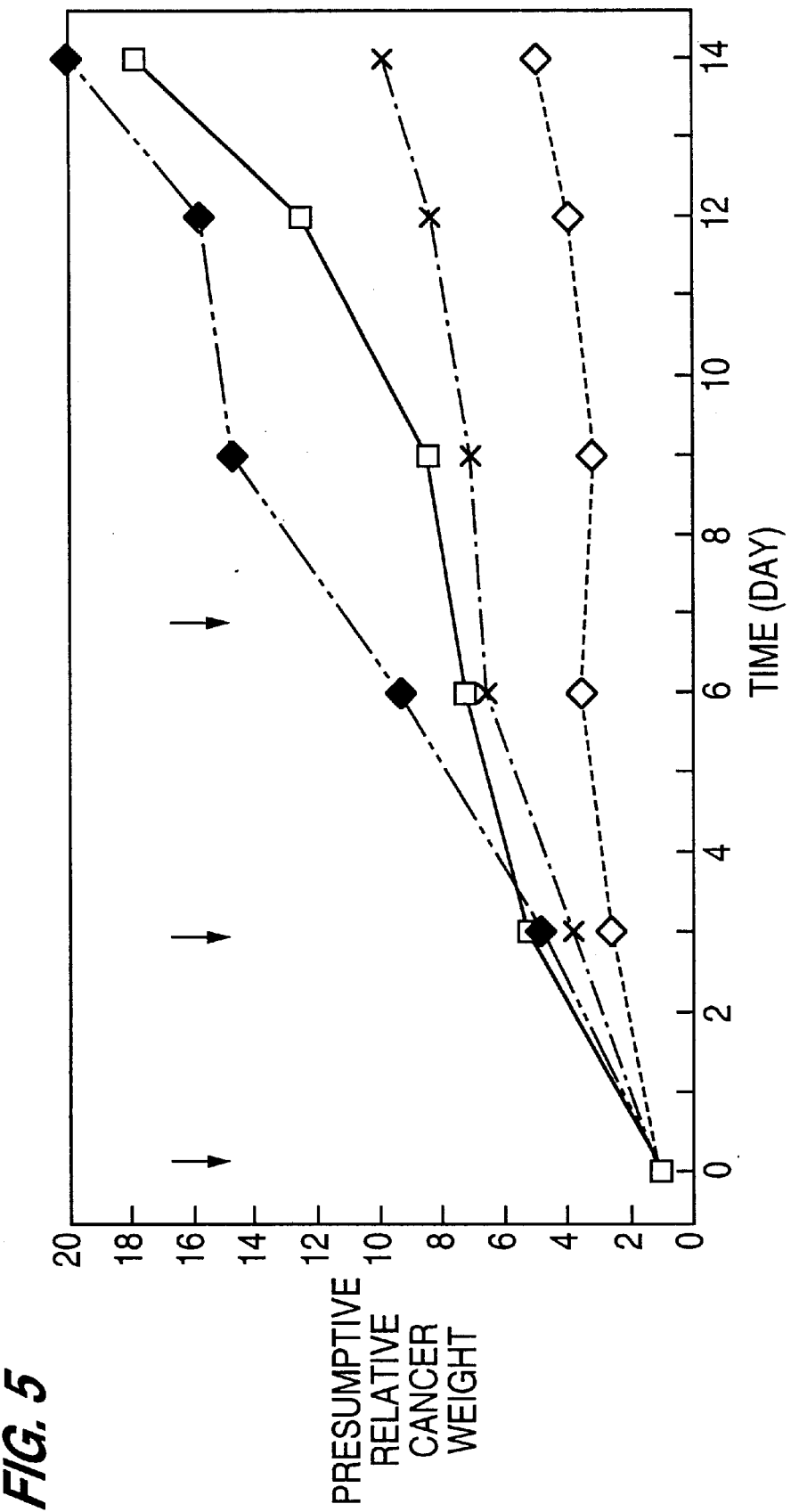
FIG. 5 shows anti-cancer effects of adriamycin-containing and PEG-modified liposome bonded to antibody GAH on the cancer transplanted to nude mouse.

Cultured MKN45 cells (1×10$^6$) were subcutaneous-transplanted to nude mouse. Experiment started when the cancer weight became about 100 $\mu$g after ten days from the transplantation (FIG. 5). Adriamycin-encapsulated liposome bonded to antibody GAH and modified with PEG was administered to mouse via caudal vein at a dose corresponding to 5 mg/kg or adriamycin day 0, 3, 7 (shown by mark ◊ in FIG. 5). As a control, phosphate buffered physiological saline (shown by mark ♦), adriamycin (shown by mark □), and adriamycin-encapsulated liposome modified with PEG (shown by mark ×) were administered to mice (each 6–7 animals). Time-course measurement of growth of cancer was conducted by means of Battle-Columbus method wherein presumptive cancer weight was determined according to the formulation: (short diameter)×(short diameter)×(long diameter)/2, and compared with that determined at the beginning of the experiment.

In FIG. 5, the abscissa shows time-lapse (days) after beginning of the experiment, and the mark (↓) indicates the administration of the pharmaceutical formulation of the invention. FIG. 5 clearly shows that the formulation of the invention, adriamycin-encapsulated liposome bonded to antibody GAH, possesses potent anti-cancer effect. It is apparent, therefore, that human monoclonal antibodies of the invention allow continuous and long term "targeting therapy" of cancer tissue or organ with the help of anti-cancer agents or toxins.

We claim:

1. A human monoclonal antibody which specifically binds to a surface antigen of a stomach cancer cell MKN 45 and colon cancer cell C-1, said antibody having a variable region of the heavy chain which is the amino acid sequence shown in SEQ ID No. 11 and a variable region of the light chain which is the amino acid sequence shown in SEQ ID No. 12.

2. A F(ab')$_2$ fragment of the human monoclonal antibody of claim 1.

3. A Fab' fragment of the human monoclonal antibody of claim 1.

* * * * *